United States Patent [19]

Rozmajzl, Jr.

[11] Patent Number: 5,415,543
[45] Date of Patent: May 16, 1995

[54] DENTAL COMPOSITE CURING APPARATUS AND METHOD

[76] Inventor: William F. Rozmajzl, Jr., 162 Tunxis Rd., Bristol, Conn. 06010

[21] Appl. No.: 169,527

[22] Filed: Dec. 20, 1993

[51] Int. Cl.$^6$ ............................................. A61C 1/06
[52] U.S. Cl. ................................... 433/29; 433/217.1; 433/226
[58] Field of Search ...................... 433/29, 217.1, 226

[56] References Cited

U.S. PATENT DOCUMENTS

| | | | |
|---|---|---|---|
| 4,645,456 | 2/1987 | James | 433/217.1 |
| 4,888,489 | 12/1989 | Bryan | 433/29 |
| 5,204,383 | 4/1993 | Manabe et al. | 433/226 |

OTHER PUBLICATIONS

R. L. Erickson, E. A. Glasspoole, and D. H. Retief, "Effect of Air Thinning on Bond Strength Measurements", *J. Dent. Res.*, 68, Special Issue, AADR Abstract #1543 (1989).

D. R. Pacropis and R. L. Ibsen, "Effect of Atmospheric oxygen on a Dentin Bonding Agent", *J. Dent. Res.*, 71 (AADR Abstracts #258) 1992.

Kirk–Othmer, *Encyclopedia of Chemical Technology*, vol. 7, fourth edition, John Wiley & Sons (1993) pp. 946–959, 1006–1022.

*Primary Examiner*—Cary E. O'Connor

[57] ABSTRACT

An improved dental apparatus for curing actinic light curable composites, primers and adhesives, incorporating in a single unit an actinic light source with an inert gas manifold and apertures for providing an inert gas blanket layer in the immediate area of the focal point of the actinic curing light, thereby giving improved bonding strengths.

18 Claims, 1 Drawing Sheet

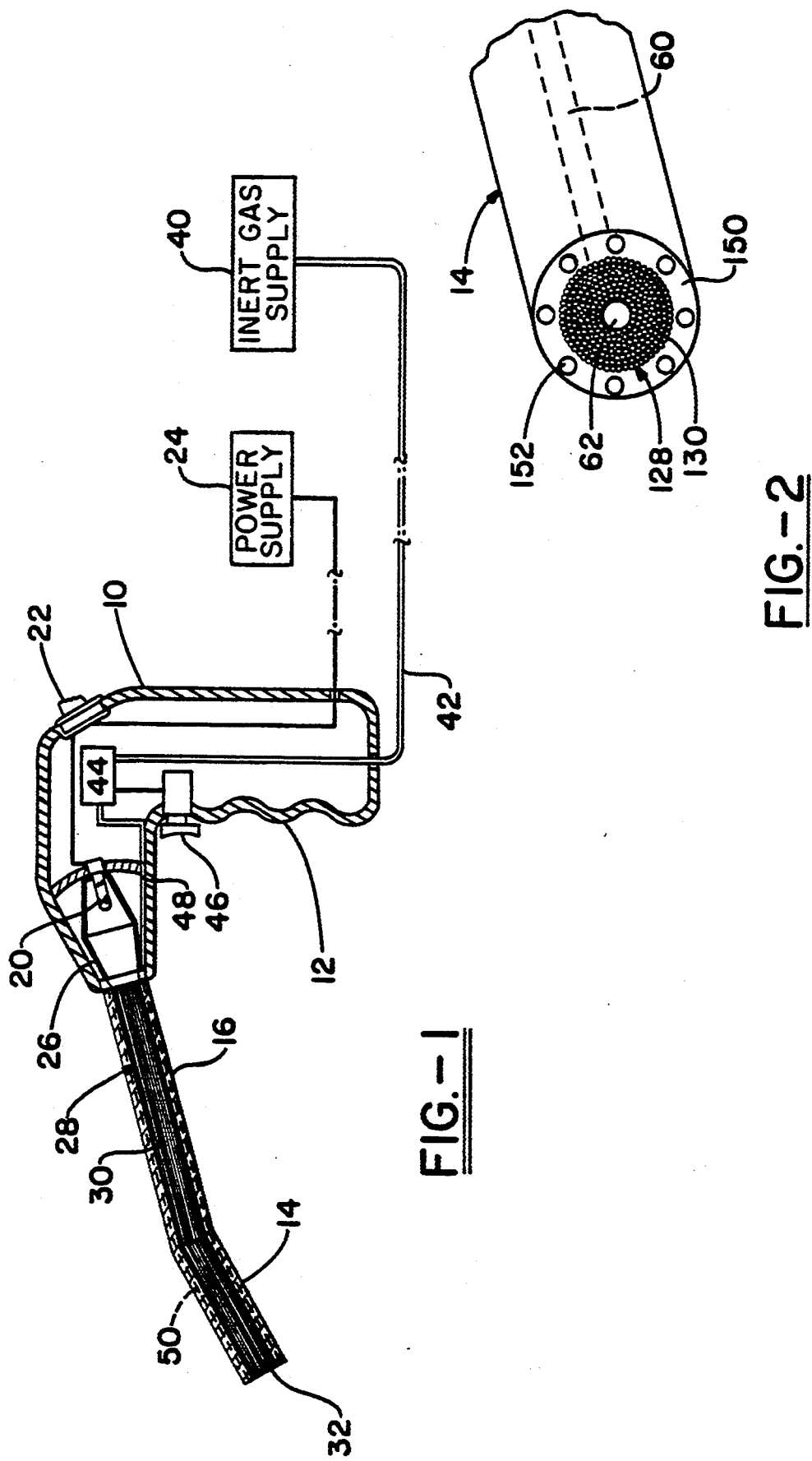

DENTAL COMPOSITE CURING APPARATUS AND METHOD

FIELD OF THE INVENTION

This invention relates to an improved dental apparatus for curing actinic light curable composites, primers and adhesives. More particularly, an inert gas blanketing device provides an inert atmosphere over the composite and/or adhesive substrate during the critical actinic curing stage to give improved bonding strengths.

BACKGROUND OF THE INVENTION

There are many systems available to the profession for bonding resin materials to mineralized tooth structures. While enamel bonding is a routine procedure, bonding to dentin is a continuing challenge and a long standing need.

There are many factors that influence the bond strengths of resin materials to dentin. The inherent characteristics of dentin are significantly different than enamel. While the composition of enamel is primarily mineralized tissue, dentin is structurally and chemically different. Acid conditioning of enamel creates a micromechanical retentive surface that produces moderate bond strengths to resin materials. Most current generation adhesive systems use a conditioner or primer on dentin to remove or modify the dentin smear layer in the bonding procedure. The primed or conditioned dentin surface is then typically treated with an adhesive resin to provide a bonding interface between the dentin and a resin restorative material. The adhesive bonding interface between dentin and a composite resin material is generally considered the weak link in the system.

There are many factors that influence the bond strength of adhesive resin materials to dentin. Generally, adhesive resins are applied in a thin layer. An object of this invention is to provide a device capable of improving the bond strengths of dentin and enamel to composite materials. A further object is to provide an apparatus capable of providing an inert gas blanket over the work area of an actinic light curable adhesive composite repair of dentin or enamel tooth surface. An advantage of the apparatus of this invention is that it can suppress oxygen inhibition of the actinic light curable adhesive and composite systems. A further advantage is that the apparatus of the invention essentially eliminates atmospheric oxygen on the surface during visible light polymerization of photocurable resin systems.

BRIEF DESCRIPTION OF THE DRAWINGS

FIG. 1 is a partially cutaway plan view of an embodiment of the inert gas curing apparatus of the invention.

FIG. 2 is a cross sectional view of the barrel portion of an alternate embodiment of the FIG. 1 apparatus.

BRIEF DESCRIPTION OF THE INVENTION

The apparatus of the invention combines in a single unit an actinic light source with an inert gas directing feature designed to allow an annular discharge of an inert gas in the immediate area of the focal point of the light source. Optionally, the devise further includes a dental syringe with the capability of a delivering an inert gas for thinning liquid layers also directed generally in the focal point of the light source. A nitrogen or argon gas source can be used with the device to produce an inert gas environment.

A preferred embodiment of the invention is an apparatus having a body having a light emitting end portion; an actinic light source positioned in said body; a light conveying means positioned in said body to convey actinic radiation from said actinic light source to said light emitting end portion; an inert gas source external to said body connected to said body by a gas conveying conduit means positioned on said body to convey an inert gas from said inert gas source to said light emitting end portion; and a gas distribution means for conveying said inert gas outside of said body proximate said light emitting end portion.

An alternate embodiment of the invention is a method of restoring a tooth in a human mouth with an actinic light curable adhesive comprising the steps of: a) cleaning and drying the portion of said tooth to be restored; b) applying an actinic light curable bonding adhesive layer to said portion of said tooth surface; c) flooding the adhesive layer and portion of said tooth to be restored with an inert gas; and d) irradiating the bonding adhesive with a hand held actinic light in the presence of the inert gas. Preferred embodiments of the method are those employing steps to thin the adhesive layer prior to curing or applying a composite material. One thinning step uses the apparatus of FIG. 2 to direct a stream of an inert gas across the surface of the actinic light curable bonding adhesive layer prior to irradiating the adhesive with the hand held light, said stream being of sufficiently high velocity to thin the adhesive layer. The second method is thinning said actinic curable adhesive prior to application with a compatible solvent or diluent suitable to reduce the viscosity of said adhesive by an amount sufficient to create a layer on said tooth at least about 10 to about 50 percent thinner than the layer formed by said adhesive in the absence of said solvent or diluent. Such solvents and diluents are those compatible with each light curable adhesive system as they are described later.

Solvents such as ketones or alcohols are useful for most systems. The thinner adhesive layer gives improved bond strengths when used with the method and/or apparatus of this invention compared to unthinned adhesive layers.

DETAILED DESCRIPTION OF THE INVENTION

The method and apparatus of this invention can be used in any area of restorative dentistry including but not limited to composite filings, caps, crowns, inlays, onlays or other cosmetic procedures involving an actinic light curable composite, primer or adhesive. Dental cements of any type which utilizes a photochemical setting mechanism solely or in combination with chemical mechanisms. Free-radical polymerization is the mechanism which is common to the materials most advantageously used in this invention. Typical dental cements are acrylic cements which are resin based composites modified for cement applications. The monomer(s) used in these cements can be simply methyl methacrylate or various types of multifunctional monomers such as BIS-GMA, triethylene glycol dimethacrylate and others. Pit and fissure sealants typically utilize the BIS-GMA or urethane dimethacrylate (UDMA) portion of the composite restorative material which has been further diluted with methyl methacrylate monomer or other low viscosity monomers and used to seal pits and fissures. Dental adhesives are the most important class of materials used in this invention along with primers and etchants used with them. Dentin adhesion can be enhanced through the use of multifunctional coupling agents that adsorb onto the dentin surface. Common type is N-(2-hydroxy-3-3-methacryloxy-propyl)-N-phenylglycine [CAS 4896-81-5] or NPG-GMA. Other conventional actinic light curable, and combination chemical and light curable, composites and adhesive/primers are within the perview of this invention without limitation. The Kirk-Othmer Encyclopedia of Chemical Technology, fourth edition, vol 7, pp 948–1012, John Wiley & Sons (N.Y. 1993) is incorporated by reference herein.

FIG. 1 shows the inert gas blanket generating actinic light curing apparatus which includes a shaped body (10) of any suitable material including metal, plastic or reinforced composite material. The body is generally hollow and adapted to hold the various elements in its interior cavity. It has a light emitting end portion (14) which includes a barrel portion (16) and preferably is pistol shaped overall with a handle portion (12) adapted for manual control.

An actinic light source (20) is positioned in the body (10). This element may be a visible, ultraviolet, infrared or laser light source depending upon the type of primer or adhesive or composite to be cured. A focusing element (26) is commonly employed to intensify the radiation from the bulb and direct it to a light conveying means, such as a fiber optic cable (28) composed of a plurality of fiber optic filaments (30, 130) having one end adjacent the actinic light source (20) and the other end terminating at the light emitting end (14) of the body (10) adapted to direct the actinic light in a desired direction. The fiber optic cable (28) conveys actinic radiation from the actinic light source (20) to the light emitting end portion (14). The emitting end (32) of the device is pointed directly at the target area containing the composite, primer or light-curable adhesive layers to be cured. The actinic radiation is emitted for a desired duration of time to optimally cure the target area.

An inert gas source (40), preferably external to the body (10) is connected to the body (10) by a gas conveying conduit tube (42) positioned on or in the body (10) to convey an inert gas from the inert gas source (40) to the light emitting end portion (14). The inert gas may be any gas which enhances the curing properties of the actinic curable adhesive, primer or composite being cured. The preferred gases are selected from the group consisting of carbon dioxide, nitrogen and the gases of Group VIIIA of the Periodic Table of the Elements.

A gas distribution means for directing and distributing the gas flow uniformly and copiously enough to effectively spread an inert gas blanket around the work area adjacent to the end (14) is a critical element of this device. A preferred form is shown in FIG. 1 and in greater detail in FIG. 2. An internal gas conduit tube (48) is connected to an annular gas conduit (50, 150) which forms the outer periphery of the barrel portion (16). The inert gas flows through the annular gas conduit (42) to a manifold at the light emitting end (14). The manifold has a plurality of bores or orifices (152) (shown in FIG. 2) annularly distributed around the fiber optic cable (28, 128). The gas flows out of the orifices (152) to form a uniform blanket of inert gas adjacent the emitting end (32) of the device. Control of the gas flow can be in any suitable manner. The trigger (46) in the handle portion (12) is adapted to be selectively manually activated to trigger a gas flow control device such as a solenoid (44) which regulates the gas flow to the conduit (50, 150) and through the orifices (152).

The switch (22) is adapted to selectively activate and deactivate the actinic light source (20) by manual means. The power supply (24) is shown in FIG. 1 as external to the device and is electrically connected to the switch (22).

The positioning of the switch or other control device is entirely optional and dependent on design parameters of the body and ergonometric considerations of the operator. The switch (22) and trigger (46) could be interchanged in location. Both control functions (gas flow and electrical activation of the actinic light source) could be accomplished with a single switch device. An automatic time lag for light activation could be incorporated to assure that the inert blanket is in place before the light source activates. This feature could be used with the single activation technique. The trigger could optionally have at least two control positions, one position for light control and another for gas flow.

FIG. 2 illustrates an alternative embodiment of the invention in which an inert gas syringe (60) is incorporated into the device. The syringe (60) would be used to desiccate the work area. It is also is useful for thinning the liquid primer or adhesive layer prior to actinic light curing. The syringe (60) has a nozzle (62) which is positioned in the device to direct the gas flow directly at the work area in a manner which will become clear in the forthcoming experimental section where thinning of the various layers of the adhesive system will be described in detail. The syringe could alternatively be positioned on the exterior portion of the barrel (16) or in the annular conduit (50, 150), so long as it could be directed to thin the layers prior to curing. The FIG. 2 embodiment shown has the nozzle (62) centered in the middle of the fiber optic tube (128). This configuration assures accurate targeting for the high speed gas jet which issues from the nozzle (62). The inert gas syringe is attached to the inert gas source by suitable conduit and is controlled by a the trigger (46) or switch (22) or a separate switch device. The multi-position switch is a preferred configuration particularly well adapted to this embodiment requiring several control modes for different functions of the device.

EXAMPLES AND EXPERIMENTAL METHODS

Dentin bonding sites were prepared on the buccal surface of 60 extracted human molar teeth by wet grinding with silicon carbide paper to 600 grit on a water cooled abrasive wheel (Ecomet III Grinder, Buehler Ltd., Lake Bluff, Ill. 60044). Three adhesive systems were used in the study: 1)Prisma Universal Bond 3 (Caulk Division/Dentsply International, Milford, Del. 19963) [Glutaraldehyde, UDMA resin, Pentac®-patented phosphite ester system ]; and 2) Scotchbond Multi-Purpose (3M Dental Products Division, St. Paul, Minn. 55144)[HEMA, BIS-GMA system], 3) Tenure Solution (Den-Mat Inc., Santa Maria, Calif. 93456)[oxilate bonding system, NPG, GMA, PMDM system]. Prisma AP.H composite (Caulk Division/Dentsply International) was used with each of the adhesive systems.

A control group of ten specimens was completed for each of the three adhesive systems as shown on Table 1. The succession of steps for each adhesive system is listed on Table 1 which follows manufacturer's recommendations. The primers (with dentin conditioner/etchant where indicated) for each system were used on the prepared dentin bonding sites followed by an application of the adhesive resin. A gelatin capsule technique was used to bond the composite cylinders to the dentin bonding sites. Composite was initially loaded into the smaller half of No. 4 gelatin capsules (Eli Lilly and Co., Indianapolis, Indiana) and the capsules were filled approximately two-thirds full. The composite was then cured in a Triad 2000 unit (York Division/Dentsply International, York, Pennsylvania) for one minute. Additional composite was added to slightly overfill the capsules. The capsules were then firmly seated on the bonding sites and any excess composite was removed using a dental explorer. The resin cylinders were visible light cured with the curing unit illustrated in FIG. 1. The light was directed at an angle of approximately 45 degrees to the intersection of the bonding sites and the composite cylinders. Three, 30 second polymerization sequences, equally divided around the circumference of the cylinders, were completed. The gelatin capsule technique resulted in a bonded composite cylinder 5.00 mm in diameter.

Ten specimens each (three adhesive systems) were also bonded in the Experimental Groups. Again, the primers (with conditioner/etchant where indicated) for each systems were used according to manufacturer's recommmendations as indicated in Table 1. The components of each adhesive system that required air thinning were thinned with a dental syringe separate from the device of FIG. 1 but attached to the inert gas source of the device using nitrogen instead of air. The adhesive resins were all thinned with nitrogen gas instead of air which is a preferred method of this invention. The adhesives were then visible light polymerized using the apparatus of FIG. 1 which supplied a continuous nitrogen flow to the resin surface. Composite was then bonded to the specimens in the experiment groups as described for the control groups. Table 1 shows the treatment steps used with each adhesive system for both the control and experimental groups.

TABLE 1

CONTROL AND EXPERIMENT GROUPS: DENTIN SURFACE TREATMENT PROCEDURES

| ADHESIVE SYSTEM | DENTIN TREATMENT | TIME | CONTROL GROUPS SURFACE TREATMENT | EXPERIMENTAL GROUPS SURFACE TREATMENT |
|---|---|---|---|---|
| Prisma Universal Bond 3 | 1) Dentin Primer | 30 sec | Air Dry | $N_2$ Dry |
|  | 2) Adhesive |  | Air Thin/VLC 10 sec | $N_2$-VLC 10 sec |
|  | 3) Prisma AP.H |  | VLC 90 sec | VLC 90 sec |
| Scotchbond Multi-Purpose | 1) Etchant | 15 sec | Rinse/Air Dry | Rinse/Air Dry |
|  | 2) Primer |  | Air Thin | $N_2$ Thin |
|  | 3) Adhesive |  | Brush Thin/VLC 10 sec | Brush Thin/$N_2$-VLC 10 sec |
|  | 4) Prisma AP.H |  | VLC 90 sec | VLC 90 sec |
| Tenure Solution | 1) Dentin Conditioner | 30 sec | Rinse/Air Dry | Rinse/Air Dry |
|  | 2) Tenure A & B |  | Air Dry (Repeat) | $N_2$-Dry (Repeat) |
|  | 3) Visar Seal |  | Air Thin/VLC 20 sec | $N_2$-Thin/$N_2$-VLC 20 sec |
|  | 4) Prisma AP.H |  | VLC 90 sec | VLC 90 sec |

VLC = Visilbe light cure
$N_2$-VLC = Nitrogen flow during visible light polymerization All the specimens were stored for 24 hours at 37 degrees C. and then vertically mounted in one inch phenolic rings with self-cure acrylic resin. Shear bond strengths were determined using an Instron machine (Model 1123, Instron, Canton Mass. 02021). A chisel-shaped rod was placed immediately adjacent and parallel to the bonding site. The composite cylinders were debonded using a crosshead speed of 5 mm/minute. The failure sites were examined to determine the location or type of bonding failure.

A Student's t-test was used for pairwise comparison of the control and experimental groups for each of the three adhesive systems evaluated.

ANALYTICAL RESULTS

The bond strength range, mean, standard deviation and percent cohesive failures in dentin are presented in Table 2. The mean shear bond strength of composite to dentin, using three adhesive systems and an ambient air atmosphere for visible light polymerization of the adhesive resins (control groups), are as follows: Scotchbond Multi-Purpose—18.8±1.5 MPa, Prisma Universal Bond 3 15.7±3.8 MPa and Tenure Solution 11.7±2.2 MPa. The mean shear bond strength for the experimental groups, using a nitrogen atmosphere during the polymerization of the adhesive resin agents, are as follows: Scotchbond MultiPurpose—22.8±2.3 MPa, Prisma Universal Bond 3—21.4±3.6 MPa and Tenure

TABLE 2

SHEAR BOND STRENGTH (MPa) AND PERCENT COHESIVE FAILURES IN DENTIN

| ADHESIVE SYSTEM | GROUP | RANGE | MEAN | STANDARD DEVIATION | PERCENT COHESIVE FAILURES IN DENTIN |
|---|---|---|---|---|---|
| SCOTCHBOND MULTI-PURPOSE | CONTROL | 16.2–19.9 | 18.2 | 1.5 | 30 |
| SCOTCHBOND MULTI-PURPOSE | EXPERIMENTAL | 19.8–28.0 | 22.8 | 2.3 | 50 |
| PRISMA UNIVERSAL BOND 3 | CONTROL | 9.4–21.4 | 15.7 | 3.8 | 40 |
| PRISMA UNIVERSAL BOND 3 | EXPERIMENTAL | 17.0–27.5 | 21.4 | 3.6 | 50 |
| TENURE SOLUTION | CONTROL | 8.0–17.0 | 11.7 | 2.2 | 0 |
| TENURE SOLUTION | EXPERIMENTAL | 15.0–25.9 | 20.6 | 3.6 | 0 |

Solution—20.6±3.6 MPa. The bond strengths of the experiment groups were significantly greater ($p < 0.05$) than the control groups for all three of the adhesive systems evaluated.

Examination of the failure sites showed a greater number of cohesive failures in dentin for the Scotchbond Multi-Purpose and Prisma Universal Bond 3 experimental groups when compared to the controls (Table 2). Three of 10 specimens (30%) in the Scotchbond Multi-Purpose control group failed in dentin and five of 10 (5%) of the experimental group specimens failed in dentin. Forty percent of the Prisma Universal Bond 3 control specimens failed in dentin compared to 50 percent of the specimens in the experimental groups. None of the Tenure Solution specimens failed in dentin in either the control or experimental groups.

The novel apparatus of this invention has been shown to be uniquely useful by making possible the heretofore unknown combination actinic light curing in the presence of an inert gas blanket. A simple hand held unit for this purpose is a significant advancement in the field of restorative dentistry. The additional optional feature of being able to thin the adhesive and/or primer layers using an inert gas syringe is a further advancement in the art of bonding composites to enamel and more importantly to dentin with high strength bond layers in a simple convenient manner. The novel method of the invention utilizes the nitrogen thinning of the adhesive/primer materials to effect superior bond strengths to those previously possible.

Without being held to the accuracy of the theory, it is felt at this time that the unexpected results shown by this inventions apparatus and method are due to the desirable properties of the inert gas to exclude oxygen molecules during the critical moments of curing and thinning. Nitrogen is the least expensive inert gas and is typical of the group and as such it will be characterized. Nitrogen is not a diradical. Nitrogen has the ability to blanket the surface of the a resin material and prohibit oxygen in the ambient air from interfering with polymerization. A nitrogen atmosphere allows the chain growth of free radicals in the polymerization of resin materials to continue without interference from oxygen. This desirable effect is believed to contribute in part to the excellent results shown in the Table 2 results.

It will be readily apparent to the skilled practitioner in the art that many modifications and changes can be made to the embodiments specifically documented herein. Such modification and changes are a part of the invention if they fall within the scope of the invention defined in the appended claims hereto.

I claim:

1. An apparatus comprising:
   a) a body having a gripping portion and a light emitting end portion;
   b) an actinic light source positioned in said body;
   c) a light conveying means positioned in said body to convey actinic radiation from said actinic light source to said light emitting end portion;
   d) an inert gas source external to said body connected to said body by a gas conveying conduit means passing through said gripping portion of said body to convey an inert gas from said inert gas source to said light emitting end portion; and
   e) a gas distribution means for conveying said inert gas from said gas conveying conduit internally of and coextensive with said light emitting ed portion over substantially the full length of said light conveying means within said light emitting end portion.

2. The apparatus of claim 1 wherein said light conveying means is a plurality of fiber optic filaments having one end proximate the actinic light source and the other end terminating at the light emitting end of said body adapted to direct the actinic light in a desired direction.

3. The apparatus of claim 1 wherein said actinic light source is selected from the group consisting of a visible light source and an ultraviolet light source affixed to the interior of said body.

4. The apparatus of claim 1 wherein said body is pistol shaped with a handle portion adapted for manual control and a barrel portion having the light emitting end forming the terminal end thereof.

5. The apparatus according to claim 4 further comprising:
   an light source activating means affixed to the exterior of said body attached to said actinic light source adapted to turn said light source on and off.

6. The apparatus of claim 5 wherein said light source activating means is a trigger positioned on the handle portion of said body and electrically attached to said actinic light source to selectively activate and deactivate said light source.

7. The apparatus of claim 1 wherein said inert gas is selected from the group consisting of carbon dioxide, nitrogen and the gases of Group VIIIA of the Periodic Table of the Elements.

8. The apparatus according to claim 1 wherein said gas distribution means comprises an annular gas conduit connected at one end to said inert gas source and the other end forming the light emitting end portion, said annular gas conduit being positioned around said light conveying means adapted to convey the inert gas flow to a manifold at the light emitting end, said manifold having a plurality of orifices annularly distributed to form the inert gas into a uniform layer adjacent the light emitting end portion.

9. An apparatus comprising:
   a) a body having a light emitting end portion;
   b) an actinic light source positioned in said body;
   c) a light conveying means positioned in said body to convey actinic radiation from said actinic light source to said light emitting end portion;
   d) an inert gas source external to said body connected to said body by a gas conveying conduit means positioned to convey an inert gas from said inert gas source to the interior of said body;
   e) a gas distribution means for conveying said inert gas from said gas conveying means over substantially the full length of said light conveying means to said light emitting end portion; and
   f) a tubular conduit connected to said inert gas source at one end with the other end forming a gas syringe terminating at the light emitting end portion of said body with a means for controlling flow of said inert gas through said tubular conduit, said tubular conduit being attached to said body such that said gas syringe directs a stream of said inert gas from said inert gas source in substantially the same direction as said actinic light.

10. A method of restoring a tooth in a human mouth with an actinic light curable adhesive comprising the steps of:
   a) cleaning and drying the portion of said tooth to be restored;
   b) applying an actinic light curable bonding adhesive layer to said portion of said tooth surface and directing a stream of an inert gas across the surface of the actinic light curable bonding adhesive layer after said layer is applied, said stream being of sufficiently high velocity to thin the adhesive layer;
   c) flooding the adhesive layer And portion of said tooth to be restored with an inert gas; and d) irradiating the bonding adhesive in said human mouth with a hand held actinic light in the presence of the inert gas.

11. The method of claim 10 wherein said bonding adhesive is selected from the group consisting of an acrylic and acrylate photopolymerizable composition.

12. The method of claim 10 wherein said inert gas is selected from the group consisting of nitrogen and the inert gases of Group VIIIA of the Periodic Table of the Elements.

13. The method of claim 10 wherein said actinic light is selected from the group consisting of visible and ultraviolet light.

14. The method of claim 10 further comprising the step of:
    etching the portion of the tooth to be restored prior to applying the bonding adhesive layer.

15. The method of claim 10 further comprising the step of:
    priming the portion of the tooth to be restored prior to applying the bonding adhesive layer.

16. A method of restoring a tooth in a human mouth with an actinic light curable adhesive comprising the steps of:
    a) cleaning and drying the portion of said tooth to be restored;
    b) thinning an actinic curable adhesive prior to applying with a compatible solvent or diluent suitable to reduce the viscosity of said adhesive by an amount sufficient to create a layer on said tooth at least about 10 to about 50 percent thinner than the layer formed by said adhesive in the absence of said solvent or diluent;
    c) applying said actinic light curable bonding adhesive layer to said portion of said tooth surface;
    d) flooding the adhesive layer and portion of said tooth to be restored with an inert gas; and
    e) irradiating the bonding adhesive in said human mouth with a hand held actinic light in the presence of the inert gas.

17. A method of restoring a tooth in a human mouth with an actinic light curable adhesive comprising the steps of:
    a) cleaning and drying the portion of said tooth to be restored;
    b) applying an actinic light curable bonding adhesive layer to said portion of said tooth surface;
    c) flooding the adhesive layer and portion of said tooth to be restored with an inert gas; and
    d) irradiating the bonding adhesive in said human mouth with a hand held actinic light in the presence of the inert gas for a sufficiently short duration, thereby forming a partially cured bonding adhesive layer.

18. The method according to claim 17 wherein said irradiating step d) is followed by the additional steps of:
    e) placing an actinic light curable composite in contact with said bonding adhesive after said irradiating step d); and
    f) curing said bonding adhesive and said composite with actinic light.

* * * * *